United States Patent [19]
Caskey et al.

[11] Patent Number: 6,015,675
[45] Date of Patent: *Jan. 18, 2000

[54] MUTATION DETECTION BY COMPETITIVE OLIGONUCLEOTIDE PRIMING

[75] Inventors: Charles Thomas Caskey; Richard A. L. Gibbs, both of Houston, Tex.

[73] Assignee: Baylor College of Medicine, Houston, Tex.

[*] Notice: This patent is subject to a terminal disclaimer.

[21] Appl. No.: 09/075,967

[22] Filed: May 11, 1998

Related U.S. Application Data

[63] Continuation of application No. 08/469,088, Jun. 6, 1995, abandoned, which is a continuation of application No. 07/710,214, Mar. 18, 1998, abandoned.

[51] Int. Cl.[7] .............................. C12Q 1/68; C12P 19/34; C07H 21/02; C07H 21/04
[52] U.S. Cl. ............................ 435/6; 435/91.1; 435/91.2; 536/23.1; 536/24.3; 536/24.31; 536/24.32; 536/24.33; 536/24.5
[58] Field of Search .............................. 435/6, 91.1, 91.2; 536/23.1, 24.3, 24.31, 24.32, 24.23, 24.5

[56] References Cited

U.S. PATENT DOCUMENTS

| | | | |
|---|---|---|---|
| 4,851,331 | 7/1989 | Vary et al. | 435/6 |
| 4,965,188 | 10/1990 | Mullis et al. | 435/6 |
| 5,578,458 | 11/1996 | Caskey et al. | 435/6 |

Primary Examiner—Jeffrey Fredman
Attorney, Agent, or Firm—Fulbright & Jaworski, LLP

[57] ABSTRACT

The present invention relates to a process for the rapid and simple detection of mutations in DNA and differences between DNA sequences. This competitive oligonucleotide priming system can be used for the detection of any differences between DNA sequences for which a DNA sequence is known.

22 Claims, 8 Drawing Sheets

MUTATION DETECTION BY COMPETITIVE OLIGONUCLEOTIDE PRIMING

This is a continuation, of application Ser. No. 08/469,088 filed Jun. 6, 1995 now abandoned. This application claims the benefits of application Ser. No. 07/170,214 filed Mar. 18, 1988 now abandoned. This application incorporates by reference the entire text of the Ser. Nos. 07/170,214, 07/769,743, and 08/469,088 applications.

FIELD OF THE INVENTION

This invention relates to the field of detecting differences (mutations) in genetic sequences by competitive oligonucleotide priming. The method of detection is useful in a variety of areas including screening for genetic disease, infectious disease, and cancer; forensic medicine; animal husbandry including breeding for agriculture and recreational purposes.

BACKGROUND

This invention is an improvement on currently established procedures for the detection of differences in DNA sequences. The detection of differences in DNA sequences is a desirable and necessary procedure in the following exemplary areas; detection and diagnosis of alleles responsible for genetic diseases in humans and other species; detection and diagnosis of DNA sequences associated or linked to genes that may or may not be involved in disease in humans and other species; detection and diagnosis of neoplasms and the effects of therapy on neoplasms; detection of and distinction between different pathogens (e.g., viruses, bacteria and fungi); determining the purity of animal strains and pedigrees; distinguishing and identifying different human and animal samples in forensic medicine.

Frequently the DNA sequence difference to be detected is a single DNA base substitution (point mutation). DNA is normally composed of various combinations of four bases termed Adenine (A); Thymidine (T); Cytosine (C) and Guanosine (G). Thus, an example of a DNA sequence may be ATCGCGATCGT. A point mutation may be the substitution of any of the three bases not normally found at a single position for a base that is normally found at that position. For example, the transmutation of a DNA sequence ATCG<u>C</u>GATCGT to ATCG<u>G</u>GATCGT is a point mutation at the underlined position.

Although point mutations may not account for the majority of differences between randomly selected DNA sequences, they do account for many differences between DNA sequences that are responsible for polymorphisms and "disease" related DNAs.

DNAs that differ only by point mutation are very difficult to distinguish by current technologies. Procedures for detecting point mutations fall into two main categories: (1) procedures which detect point mutations when the precise DNA sequence change can be anticipated; (2) procedures which "scan" for point mutations where the precise nature of the individual DNA gene change is not known. The present invention will work in either situation.

Prior to the present invention, point mutations where there is some knowledge of the DNA sequences differences between the normal and variant DNA have been detected by:

(1) Restriction fragment length polymorphisms (D. Botstein, et al. Am. J. Hum. Genet., 32:314–331 (1980)) or (2) Allele specific oligonucleotide (ASO) probing (G. Angelini, P.N.A.S. (USA), 83:4489–4493 (1986).

In the restriction fragment length polymorphism procedure, restriction endonucleases are used to cut the DNA into various chain lengths which can be measured. In allele specific oligonucleotide probing, single base mismatches are determined by thermodynamic differences. The annealing conditions are set such that perfectly paired strands anneal and non-perfectly paired strands do not anneal.

The polymerase chain reaction (PCR) exemplified by U.S. Pat. Nos. 4,683,202 and 4,683,195 is used to amplify specific DNA sequences, however, PCR does not, by itself, provide a method to detect single base mutations. The PCR may be used in conjunction with other techniques such as the present invention to detect point mutations and other DNA sequence differences.

The current invention, competitive oligonucleotide priming (COP), distinguishes closely related DNA sequences by comparing competitive annealing of two or more DNA sequences closely matched to the DNA sequence of interest. The COP procedure has some similarity to the Allele specific oligonucleotide probing procedure and to the polymerase chain reaction procedure, however, neither ASO probing or PCR amplification procedures utilize the unique competitive annealing assay of the present invention to detect specific sequences differing by a single base.

The COP procedure of the present invention has the advantages of simplicity and speed. Furthermore, no filter for hybridization is needed, it can be used with solid supports and the whole procedure can be automated for decreased cost. It provides a method to solve a long felt need to improve and simplify the detection of single base changes in DNA sequences.

SUMMARY OF THE INVENTION

An object of the present invention is a method for detecting a specific known polynucleotide sequence.

An additional object of the present invention is a method for distinguishing between different nucleotide sequences.

A further object of the present invention is the detection of genetic disease.

An additional object of the present invention is a method to detect genetic polymorphism in known genetic sequences.

Thus, in accomplishing the foregoing objects there is provided in accordance with one aspect of the present invention a method for detecting the presence or absence of a specific known nucleic acid sequence or distinguishing between different sequences comprising the steps of:

adding competitive oligonucleotide primers to a sample of nucleic acid or mixture of nucleic acids, wherein said competitive oligonucleotide primers include at least two primers, one being substantially complementary to the specific known sequence and at least one having a base mismatch with the specific known sequence;

preferentially hybridizing the substantially complementary primer to the specific known sequence under competitive conditions;

extending the preferentially hybridized primer from its 3' terminus to synthesize an extension product complementary to the strand to which the primer is hybridized; and identifying said extension product.

Additional embodiments of the invention include attaching labels to the competitive oligonucleotide primers for the easy detection of the extension products. These labels include radioisotopes, fluorescers, chemiluminescer, enzymes and antibodies.

In other embodiments, the sequence to be detected is amplified during the competitive oligonucleotide primer assay and/or prior to performing the competitive oligonucleotide primer assay.

A further embodiment employs multiple competitive oligonucleotide primers each labeled differently to simultaneously detect genetic polymorphism at a single locus or to detect different loci.

Another embodiment includes using the competitive oligonucleotide primer method in detecting genetic disease, forensic medicine, paternity testing, gene mapping, pathogen detection and neoplasia screening and therapy.

An additional embodiment includes dividing a sample of nucleic acid from an individual and performing competitive oligonucleotide primer assays simultaneously on the different portions.

The present invention is useful in detecting genetic polymorphisms. Specific applications include: detecting genetic diseases such as sickle cell anemia, $\alpha_1$-antitrypsin deficiency and hemophilia; screening for disease association by linkage analysis; tissue typing; gene mapping; screening for neoplasms and the effect of therapy; detection of known pathogens, (for example viruses bacteria, yeast and fungi); determining the pedigrees and/or purity of animal strains; and disease screening in animals.

Other and further objects features and advantages will be apparent from the following description of the presently preferred embodiments of the invention given for the purpose of disclosure when taken in conjunction with the accompanying drawings.

BRIEF DESCRIPTION OF THE DRAWINGS

The invention will be more readily understood from a reading of the following specification and by references to the accompanying drawings, forming a part thereof:

FIG. 1 demonstrates the basic principle of the competitive oligonucleotide priming system;

FIG. 2 DNA sequence of regions surrounding the oligonucleotide priming sites in Examples 1 and 2.

The drawings are not necessarily to scale and certain features of the invention may be exaggerated in scale or shown in schematic form in the interest of clarity and conciseness.

DETAILED DESCRIPTION

It will be readily apparent to one skilled in the art that various substitutions and modifications may be made to the invention disclosed herein without departing from the scope and spirit of the invention.

The term "oligonucleotide primers" as used herein defines a molecule comprised of more than three deoxyribonucleotides or ribonucleotides. Its exact length will depend on many factors relating to the ultimate function or use of the oligonucleotide primer including temperature, source of the primer and use of the method. The oligonucleotide primer can occur naturally as in a purified restriction digest or be produced synthetically. The oligonucleotide primer is capable of acting as a point of initiation of synthesis when placed under conditions which induce synthesis of a primer extension product complementary to a nucleic acid strand. The conditions can include the presence of nucleotides and an inducing agent such as DNA polymerase at a suitable temperature and pH. Although the primer preferably is single stranded, it may alternatively be double stranded. If it is double stranded, the primer must first be treated to separate its strands before it is used to produce extension products. In the preferred embodiment, the primer is an oligodeoxyribonucleotide. The primer must be sufficiently long to prime the synthesis of extension products in the presence of the inducing agent. In the competitive oligonucleotide primer method, oligonucleotides can range from about 8 to 30 mers in length. In the preferred embodiment, the competitive primers are 12 to 16 mers in length. The sensitivity and specificity of the competitive oligonucleotide primer assay is determined by the length. Primers which are too short, i.e., less than about 8 mers show non-specific binding to a wide variety of sequences in the genome and thus are not very useful. On the other hand, primers which are too long, i.e., greater than about 30 mers do not show competitive binding because a single base mismatch usually does not affect the binding efficiency in long oligonucleotides.

As used herein "competitive oligonucleotide primers" shall refer to those oligonucleotide primers which differ by at least one base mismatch. This difference or differences results in a differential rate and ability to bind to the known nucleotide sequence. By controlling the rate and ability to bind the competitive oligonucleotide primer can be advantageously used. A variety of conditions including temperature, ionic strength and the chemical composition of the buffer will alter the binding capacity. Under appropriate conditions, when competitive oligonucleotide primers are incubated with a DNA template, the oligonucleotide sequence which most nearly matches the known sequence to be hybridized will bind preferentially over the sequence which has a base mismatch or the most base mismatches.

As used herein "base mismatch" shall refer to a change in the nucleotides, such that when a primer lines up with the known sequence an abnormal bonding pair of nucleotides is formed. Normally guanine (G) and cytosine (C) bind and adenine (A) and thymine (T) bind in the formation of double stranded nucleic acids. Thus, the standard base pairing, A-T or G-C, is not seen in base mismatched pairing. A variety of base mismatches can occur, for example G-G, C-C, A-A, T-T, A-G, A-C, T-G, or T-C. This mispairing, and its effects on the efficiency of annealing is one basis for the competitive binding of the oligonucleotide primers.

As used herein a "common primer" is a primer which binds to the strand complimentary to the strand that the competitive oligonucleotide primers bind and it binds at a site distant from the competitive oligonucleotide primers. This distance should be sufficient to allow the synthesis of extension product between the two binding sites, yet close enough such that the extension products of the common primer(s) overlap the competitive oligonucleotide primer(s) and the extension product of the competitive oligonucleotide primer(s) overlaps the common primer(s). The extension products from the common primer(s) and competitive primer(s) are complementary to each other.

Figure 1A:
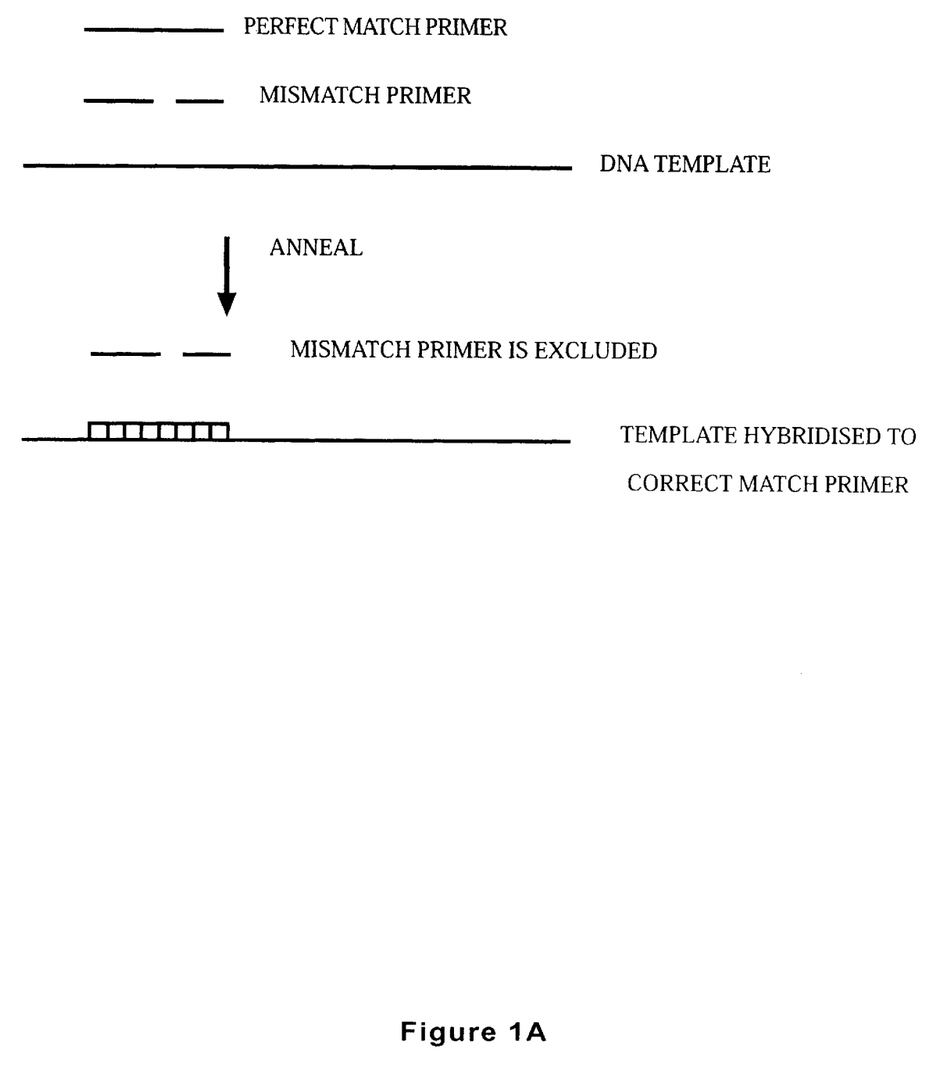
FIG. 1A demonstrates that when two closely related primers compete for a single DNA template, a perfectly matched primer will anneal or hybridize with the template in preference to a primer with a single base mismatch.

All the oligonucleotide primers used herein are selected to be substantially complementary to the different strands (templates) of each known specific sequence to be detected so that the primers hybridize with their respective strands. The primer sequence need not reflect the exact sequence of the template in the competitive oligonucleotide primer assay. However, it is important that the different sequences used as competitive oligonucleotide primers have different numbers of base mismatches. For example, in the detection of a normal genetic sequence, the competitive oligonucleotide primers could include a primer which is an exact copy of the complementary strand to the normal genetic sequence and a primer which is a copy of the complementary strand with one base pair mismatched (see FIG. 1A). Both a perfectly matched primer and a primer with a single DNA base mismatch are able to bind to the template. However, when the two closely related primers are incubated together with the DNA template, the binding of the perfectly matched primer will be favored over a primer with a single base mismatch. Alternatively, one of the primers can contain one base mismatch to the known genetic sequence and the other oligonucleotides would contain at least two mismatches. Thus, generally the requirements are that one of the sequences have N mismatches and the other sequence or sequences have greater than N mismatches, where N can be from zero to any number of mismatches which will still provide a substantially similar sequence able to bind. When two oligonucleotides differing by a single DNA base are supplied as primers in a reaction containing a single DNA or RNA template then the perfectly matched oligonucleotide primer will be highly favored over the primer with the single base mismatch. Similarly, if neither primer is a perfect match the more closely matched primer will be favored. The greater the difference between the sequence of interest and the other sequences, the more efficiently the competitive oligonucleotide primer assay functions. However, when the difference is too great, it may no longer function as a competitive assay.

As used herein the term "genetic polymorphism" refers to the variation seen at a genetic locus wherein two or more different nucleotide sequences can coexist at the same genetic locus in the DNA. The different sequences may or may not result in disease. For example, HL-A haplotypes have different genetic sequences which vary but do not result in disease while sickle cell anemia is a disease caused by a single change in the genetic sequence.

As used herein the "normal genetic sequence" refers to that sequence, which in the case of genetic disease results in the normal phenotype, or in the case of no disease results in the most common haplotype found in the population.

As used herein the "mutated genetic sequence" refers to that sequence which has at least one base change difference in the DNA sequence from the normal genetic sequence. The mutant sequence or sequences are responsible for the genetic disease or the less common haplotypes expressed at a given locus.

As used herein the term "extension product" shall be that product which is synthesized from the 3' end of the oligonucleotide primer and which is complementary to the strand to which the oligonucleotide primer is bound. A "Competitive extension product" shall refer to the extension product which-is synthesized from the 3' end of one of the competitive oligonucleotide primers.

As used herein the term "differentially labeled" shall indicate that the each competitive oligonucleotide primer has a different label attached. One skilled in the art will recognize that a variety of labels are available. For example, these can include radioisotopes, fluorescers, chemiluminescers, enzymes and antibodies. Various factors affect the choice of label. These include the effect of the label on the rate of hybridization and binding of the primer to the DNA, the sensitivity of the label, the ease of making the labeled primer, ability to automate, available instrumentation, convenience and the like. For example, in the methods employing differentially labeled primer, each primer could be labeled with a different radioisotope such as $^{32}P$, $^{3}H$ and $^{14}C$ or each primer could be labeled with a different isotope of the same element; a different fluorescer such as fluorescin, tetramethylrhodamine, Texas red and 4-chloro-7-nitrobenzo-2-oxa-1-diazole (NBD); or a mixture of different labels such as radioisotopes, fluorescers and chemiluminescers. In these examples, each primer can be differentiated from all other primers when they are in a mixture.

The specific known nucleic acid sequence which is being detected herein may be derived from any source(s) in purified or non-purified form. Sources can include plasmids and cloned DNAs, genomic DNA from any source including bacteria, fungi, yeast, viruses and higher organisms such as plants, birds, reptiles and mammals. In the preferred embodiment, the source is genomic DNA. The genomic DNA can be prepared from blood, urine, tissue material, such as chorionic villi and amniotic cells, by a variety of techniques known to one skilled in the art.

Any specific known nucleic acid sequence can be detected by the present method. It is only necessary that a sufficient number of bases at both ends of the sequence be known in sufficient detail to prepare two oligonucleotide primers which will hybridize to the different strands of the desired sequence at relative positions along the sequence. After hybridization of the primers, an extension product is synthesized from one primer. When the extension product is separated from its template, it can serve as a template for extension of the other primer into a nucleic acid of defined length. The greater the knowledge about the bases at both ends of the sequence, the greater can be the specificity of the primers for the targeted nucleic acid sequence, and thus, the greater the efficiency of the process.

The oligonucleotide primers may be prepared using any suitable method, for example, the phosphyltriester and phosphyldiester methods or automated embodiments thereof, the synthesis of oligonucleotides on a modified solid support, the isolation from a biological source (restriction endonuclease digestion), and the generation by enzymatically directed copying of a DNA or RNA template.

One embodiment of the present invention is a method for detecting the presence or absence of a specific known nucleic acid sequence, or distinguishing between different sequences, comprising the steps of: adding competitive oligonucleotide primers to a sample of nucleic acid or a mixture of nucleic acids, wherein said competitive oligonucleotide primers include at least two primers, one being substantially complementary to the specific known sequence and at least one having a base mismatch with a specific known sequence; preferentially hybridizing the substantially complementary primer to the specific known sequence under competitive conditions; extending the preferentially hybridized primer from its 3' terminus to synthesize an extension product complimentary to the strand to which the primer is hybridized; and identifying the extension product.

According to the present invention, two closely related DNA sequences may be distinguished by competitive oligonucleotide priming.

Basically, in order to detect a DNA sequence which differs by one or more bases from a known DNA sequence, oligonucleotide primers which match the known DNA sequence and oligonucleotide primers which differ from the matched oligonucleotide primers by at least one base pair are incubated in the presence of the DNA to be tested. At least one of the primers may be detectably labeled as described below. The assay of the present invention detects the preference for more closely matched DNA primers to anneal or hybridize to its corresponding template by determining which of the labeled primers is incorporated into the extension product.

For example, the reaction conditions can include two oligonucleotide primers, preferably in at least a molar excess of primer to template. The deoxyribonucleoside triphosphates dATP, dCTP, dGTP and TTP are added in adequate amounts to provide sufficient substrate for the synthesis of the new DNA strands and at concentrations sufficient for the activity of the polymerase to be used. The resulting solution is heated to about 100° C. for from about 15 seconds to about 2 minutes and preferably about 1 minute in order to denature any double stranded species. A variety of buffers can be used to support the competitive hybridization. It is required that the stringency of the buffer conditions is such that the best matched primer is able to bind efficiently to allow DNA extension. The buffer must also allow the enzymes that catalyze the DNA extension to function. The amount of the primer that is present must be greater than the molar amount of the template that is present, however it is not necessary that each of the primers are present in the same molar amount.

The length of the denaturation period may vary. It is only necessary that it be sufficient to allow denaturation of any double stranded template species in the mixture. The temperature at which the denaturation is carried out may also vary depending upon the other denaturation conditions such as, buffer constituents, length of denaturation period, level or concentration of double stranded components in the mixture, and physical characteristics, such as melting temperature, of the double stranded component(s). Preferably, the temperature for the denaturation process ranges from about 90° C. to 110° C.; most preferably, the denaturation is carried out at about 105° C.

After the denaturation is complete, the solution is allowed to cool and the primers are allowed to hybridized (or anneal) to the template strands under competitive conditions. The annealing temperature may vary from about 10° C. to 65° C., preferably, 28° C. The ideal temperature may be determined according to methods known to those of skill in the art and will be dependent upon factors such as the melting temperature of the best match primer, as well as the other assay conditions described above. The annealing process is allowed to proceed for at least 5 seconds. Preferably, the annealing process is carried out at 28° C. for 30 seconds.

After the annealing process is complete, an inducing or catalyzing agent is introduced into the solution to start the primer extension reaction. The inducing or catalyzing agent may be any agent that promotes the extension of the oligonucleotide primer, such as the Klenow fragment of DNA polymerase 1 from *E. coli* or the heat-stable DNA polymerase from *Thermus aquaticus* (*Taq* polymerase). The amount of catalyzing agent added will depend upon the inherent activity of the preparation and will be known to one of skill in the art. For instance, when the *E. coli* Klenow fragment is used as the catalyzing agent, at least 0.1 to 100 Units. One unit of Klenow activity may be defined as that amount of enzyme that will catalyze the incorporation of 10 nM of total deoxyribonucleotides into acid precipitable material in 30 minutes at 37° C. using poly[d(A-T)] as template-primer. Preferably, 5 Units are added. Various conditions are known to one skilled in the art, but the extension reaction can occur at 8° C. to 90° C. using, for example, DNA polymerase (Klenow) or heat stable DNA polymerase (*Taq*). The extension reactions are usually done in a final volume of 100 microliters containing 30 mM Tris-acetate, pH 7.9, 60 mM sodium acetate, 10 mM magnesium acetate, 10 mM dithiothreitol, 1.5 mM each of the DATP, TTP, dCTP and dGTP, 4 $\mu$M of each primer or primer family and about 0.5 to 1 $\mu$M of DNA.

Depending on the method used to identify the extension product, the steps involved will vary. For example, if the common primer is attached to a solid support, the sequences of the extension primer binding to the known sequence will be bound to the solid support. Thus, detecting the presence or absence of a sequence on the solid support will allow identification of the primer. On the other hand, if the primers are not attached to a solid support, it may be necessary to treat the double stranded extension product-template to form single strands. One skilled in the art will recognize that physical, enzymatic and chemical means are available to separate the strands. Typically heat denaturation is used.

Figure 1B:
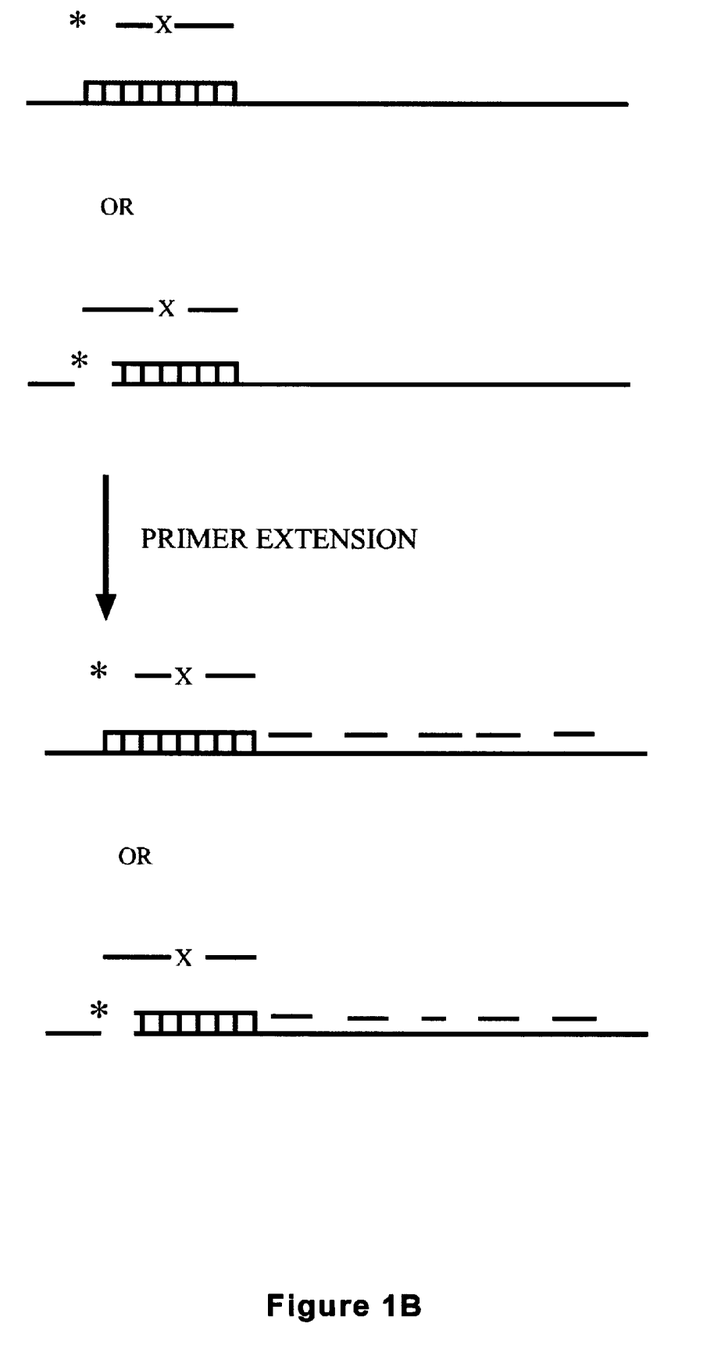
FIG. 1B demonstrates that an oligonucleotide primer can be made radioactive to facilitate its detection.

A variety of methods are known in the art for the detection of nucleic acid sequences. For example, nucleic acid sequences can be labeled with radioisotopes, fluorescers, chemiluminescers, enzymes and antibodies. The presence or absence of the label indicates whether the extension product is from that specific primer (FIG. 1B). Alternatively, the sequence of interest could contain a restriction endonuclease site which is different in the normal and mutated sequences. In this case the double stranded extension product-template would not be separated, but rather would be submitted to restriction endonuclease digestion and the resultant restriction fragment lengths measured.

Figure 1C:
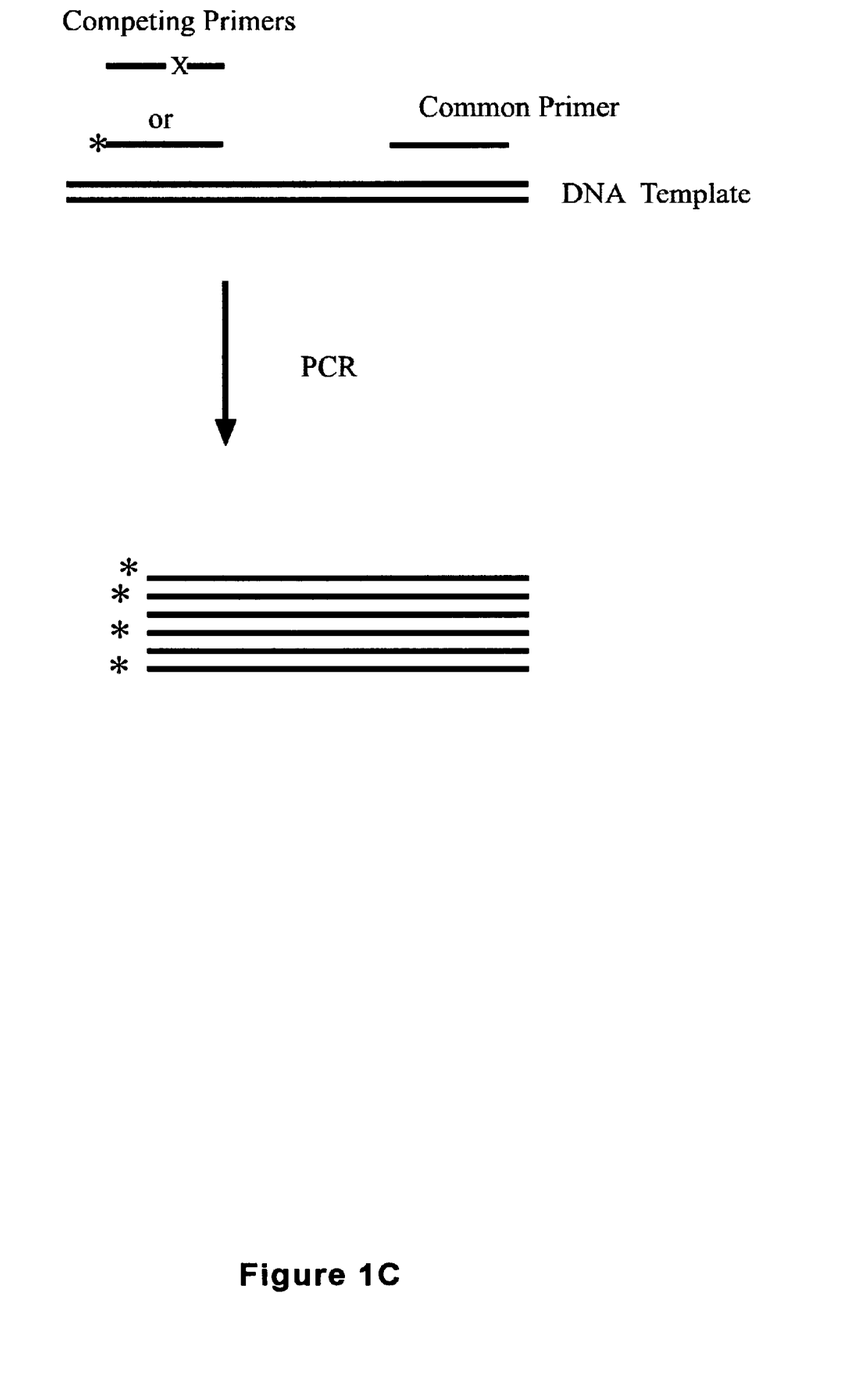
FIG. 1C the demonstrates detection of competitive oligonucleotide priming by the polymerase chain reaction (PCR). A DNA template is primed at two sites. A single oligonucleotide primer is used at one of the sites (common primer) and the competing oligonucleotide primers are used at the other site, which includes the DNA mutation. After PCR amplification, the 'correct', perfectly matched primer is incorporated into the PCR amplification product.

Another embodiment of the method includes the further step of amplifying the extension products prior to the identifying step. The amplification includes adding a common primer and repeating at least once: (1) separating the extension product from its complementary strand, (2) preferentially hybridizing the primers, and (3) extending the hybridized primers. The steps of the amplifying method can be repeated indefinitely. The number of repetitions is limited by the amount of competitive primers, common primers and deoxynucleotides. The extension products increase exponentially. This process can be seen in FIG. 1C. This process can be used to increase the sensitivity by increasing the number of sequences to be detected. Thus, there is enhancement of the sequence of interest versus the background.

Alternatively, it may be advantageous to enhance the sequence of interest prior to an addition of the competitive oligonucleotide primers. The method of amplifying a sequence is described in "Process for Amplifying Nucleic Acid Sequence" U.S. Pat. No. 4,483,202 and "Process for Amplifying, Detecting, and/or Cloning Nucleic Acid Sequences" U.S. Pat. No. 4,683,195, both of which are herein incorporated by reference. Basically this method comprises the steps of: annealing an oligonucleotide primer to each strand of each different specific sequence; extending the primer from its 3' terminus under conditions which synthesize an extension product complementary to each strand, said extension product after separation from its complement, serving as a template for synthesis of the extension product of the other primer; separating the primer extension product from the templates on which they were synthesized to produce single stranded molecules; and amplifying the specific sequence by repeating the annealing, extending and separating steps at least once.

After the amplification has occurred, the competitive oligonucleotide primers can be added and the competitive oligonucleotide primer method as previously described is followed.

A major distinction and advantage of the present invention over the previous references is the competitive nature of the binding between the substantially complementary sequence and that containing at least one more base mismatch. For example, the Allele specific oligonucleotide (ASO) probing method of point mutation detection uses oligonucleotides as hybridization probes, not primers. The different ASO probes are used in separate reactions and are not held in competition.

One of the ways that the COP procedure differs from the PCR procedure is that PCR uses pairs of opposing primers acting at different sites to amplify specific DNA sequences while COP uses sets of primers at a single site, to compete for binding. In the PCR procedure, more than two oligonucleotide primers may be present and these may be used to amplify different sites in the same reaction vessel. Additionally, the PCR may use primers that are not perfectly matched to the DNA template, but are only 'substantially complementary.' However, the PCR does not utilize mixtures of primers that compete for a single binding site on the polynucleotide template in such a way that if the most favored competing oligonucleotide primer was not present, the next most closely matched competing primer would bind and prime the DNA synthesis at the same site. Thus, it is the ability of competitive oligonucleotide primers to each function as primers for DNA synthesis from a common site, but the prevalence of incorporation of the best-matched primer, that makes the COP unique. The differential labeling of the individual competitive oligonucleotide primers allows the competition event to be monitored, and thus the DNA sequence of the template can be inferred by knowing the oligonucleotide primer that is best matched.

Another major distinction from prior methods is the fact that short primers, about 12 mers, can be more readily used for the competitive oligonucleotide primer assay, whereas it is usually desirable to use longer primers for the amplification process. Because of the sensitive nature of the base mismatch assay, the longer primers, usually used for amplification, may not be as effective in a competitive assay.

The competitive oligonucleotide priming assay may function in situations where the precise DNA sequence to be tested is not known. A minimum requirement is sufficient DNA sequence information to allow the synthesis or derivation of an oligonucleotide primer that will bind to and prime DNA synthesis on the normal DNA template. Competitive oligonucleotide primers may be used that differ from the oligonucleotide primers that bind to the normal DNA template. Provided any one primer is labeled in a way that it may be distinguished from other competing oligonucleotide primers, then the competition between the labeled primer and other primers may be monitored by the incorporation of the label into the DNA extension product.

The competitive oligonucleotide priming procedure can be used for a variety of purposes. It can be used to detect known genetic sequences. One application is the detection of genetic disease. Any genetic disease for which the mutation(s) is known and the surrounding nucleotide sequence is known can be detected by this procedure. For example, in sickle cell anemia a single base change results in the genetic disease. The mutation and surrounding sequence are known and thus the competitive oligonucleotide primer method can be used to detect sickle cell anemia. Since the competitive oligonucleotide method is a relatively simple, quick, inexpensive and accurate assay, it should become the method of choice for diagnosis. For example, from the time the sample is taken until the result is known takes only about 6 hours.

Other diseases including thalassemia, ornithine transcarbamylase deficiency, hypoxanthine-guanine-phosphoribosyl-transferase deficiency, and phenylketonuria can easily be detected using this process. This method can be applied to cells acquired by biopsy, amniocentesis or as chorionic villi. Because the procedure measures DNA base changes directly, there are no limits as to the developmental time or tissue which must be assayed. The only requirement is that there be a known sequence at the site that the primers will bind. This advantage can be readily appreciated in a disease like phenylketonuria which is normally only expressed in the liver. The present method allows the detection of phenylketonuria in amniotic fluid, chorionic villi or blood without requiring a liver biopsy. Thus, one skilled in the art will readily recognize the tremendous advantages in speed, time, safety and ease of running the assay of the present method.

Other applications can be readily visualized. For example, paternity testing by testing genetic polymorphism's at any number of loci with known sequences. With the competitive oligonucleotide primer method a different label could be used for each locus and thus a variety of different loci could be tested at the same time. Similarly, the competitive oligonucleotide primer method can be used for gene mapping and linkage analysis. Thus, even if the gene itself was not known but a closely associated sequence with a polymorphism was known, the competitive oligonucleotide primer method could be used to detect the genetic diversity at the associated sequence and to make a diagnosis.

Another area in which the method would have wide utilization is in forensic medicine. In forensic medicine, detection of genetic variation is used to provide a method to determine the origin of the sample. The competitive oligonucleotide primer method provides a quick and accurate method to determine the sequences of a number of genetic loci from the same sample.

The addition of extra genetic material to a genome can also be detected by the competitive oligonucleotide primer method. For example, various infectious diseases can be diagnosed by the presence in clinical samples of specific DNA sequences characteristic of the causative microorganisms. These include bacteria from classes such as Salmonella, Streptococcus, Staphylococcus bacilius; all fungi; all yeast; and viruses such as cytomegaloviruses, herpes simplex type I and II and HIV (Aids virus) which result in infectious disease. Again, the quick, relative, easy nature of the competitive oligonucleotide primer method allows a ready procedure for the detection of diseases. Because of the small quantity of many of these microorganisms in a biological sample, it may be necessary to amplify the sequences of interest using the PCR procedure described in U.S. Pat. Nos. 4,683,195 and 4,683,202 prior to applying the competitive oligonucleotide primer assay of the present invention.

Another important use of this procedure is in the detection of neoplasms and the monitoring of the therapy of the neoplasm. Because many neoplasms result in the mutations of genetic sequences in the genome of the host or the insertion of known sequences, the competitive oligonucleotide primer method can be used to detect these sequences. Although detection of neoplasms is important, even more useful is the monitoring of the therapy. After the institution of therapy, whether it be by drugs surgery or radioactivity, successful neoplastic therapy results in the disappearance of the sequence associated with the disease. Thus, after therapy has started, samples could be taken and the competitive oligonucleotide primer method used to follow the course and the effectiveness of therapy. This would provide a better prognosis for recurrence, since very small amounts of the sequence can be detected, the test is relatively quick, and multiple samples can be monitored over time.

In addition to the many uses of the competitive oligonucleotide primer method in humans, there are also extensive opportunities for the use of the procedure in animals. In many cases, for example, horse racing and breeding stock, in cows, pigs, dogs, cats and other animals, the competitive oligonucleotide primer method could be used to determine the purity of the strain. Since determining the purity of the strain is a measure of the sameness of the genetic sequence, and since the competitive oligonucleotide primer can be used to quickly and rapidly measure genetic sequences, it can be used as an accurate measure of the purity of the strain in animals. As in humans, the competitive oligonucleotide primer method can also be used for pedigree analysis and disease screening in animals. Again, this would be important in animal husbandry, for example, race horses, bull breeding, milk and beef breeding, chicken breeding and pig breeding programs. In addition, since disease states may be accurately and quickly determined, the length of quarantine for imported animals could be substantially diminished.

The following examples are offered by way of illustration and are not intended to limit the invention in any manner. In these examples all percentages are by weight, if for solids, and by volume, if for liquids, and all temperatures are in degrees Celsius unless otherwise noted.

EXAMPLE 1

DETECTION OF A C TO A POINT MUTATION IN MURINE ORNITHINE TRANSCARBAMYLASE COMPLEMENTARY DNA (cDNA).

Figure 2A:
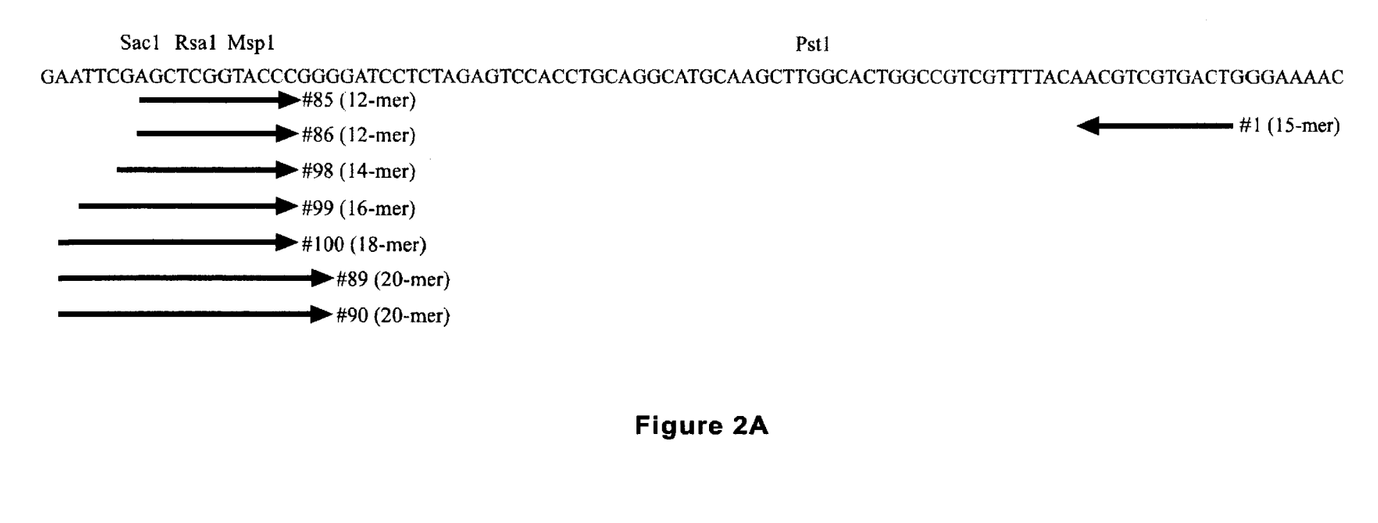
FIG. 2A shows the M13mp18 filamentous phage DNA sequence.
Figure 2B:
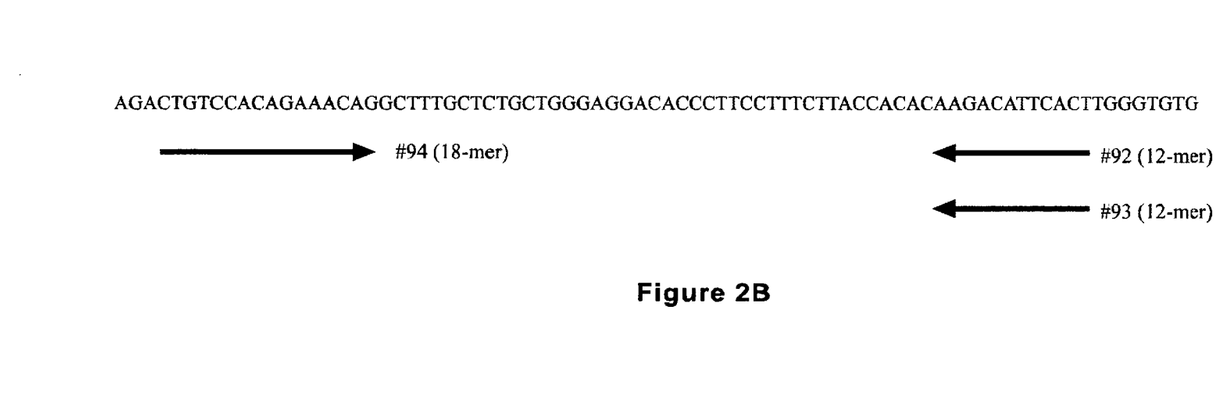
FIG. 2B shows the ornithine transcarbamylase CDNA sequence.

An example of point mutation detection by the competitive oligonucleotide primer method is demonstrated using cloned cDNA sequences from the murine ornithine transcarbamylase OTC gene (Veres et al. Science 237 415 (1987)). The target sequences are cloned cDNA from normal OTC mice, and mutant OTC cDNA from OTC deficient "sparse fur" mice, that are identical except for the substitution of an A:T base pair for a C:G base pair at a previously determined position. Two oligomers (12-mers), complementary to either the (+) or (spf) cDNA sequences were synthesized and are shown in Table 1 as #92 and #93, respectively. The complete DNA sequence of the region surrounding the primer binding sites is shown in FIG. 2B.

TABLE 1

OLIGONUCLEOTIDE PRIMERS

| No. | Sequence (5' to 3')[a] | Length | Template |
| --- | --- | --- | --- |
| 1 | CCCAGTCACGACGTT | 15 | M13 common |
| 85 | AGCTCGGTACCC | 12 | M13 COP |
| 86 | AGCTCGG(TA)AC(CG)C | 12 | " |
| 89 | AATTCGAGCTCGGTACCCGG | 20 | " |
| 90 | AATTC(GC)AGCTCGG(TA)AC(CG)CGG | 20 | " |
| 92 | CAAGTGAATGTC | 12 | OTC (+) |
| 93 | CAAGTTAATGTC | 12 | OTC (spf) |
| 94 | CTGTCCACAGAAACAGGC | 18 | OTC common |

[a]Parentheses denote mixed oligonucleotides at a single position.

The DNA templates used in this example differ by a single DNA base pair change. The two primers, #92 and #93, were employed along with a third, common oligonucleotide primer, #94, that was in opposite sense to the two competing primers (#92 and #93). The #92 and #93 primers are 12 mers in length and #94 is an 18 mer in length. Duplicate reactions were performed in which either the #92 or #93 oligomer was radiolabelled with $^{32}P$. In these reactions the primers #92 and #93 competed to detect the presence of the spf mutation. Primer #94 was the common primer in the reaction.

A total of four reactions were performed: (1) normal template combined with radiolabelled normal primer and unlabelled mutant primer; (2) normal template combined with unlabelled normal primer and radiolabelled mutant primer; (3) mutant template combined with radiolabelled normal primer and unlabelled mutant primer; and (4) mutant template combined with unlabelled normal primer and labelled mutant primer. Thus, the chemical composition of all four reactions was similar, except that either the normal or mutant template was present with a radiolabel present in either the normal or mutant competing primers.

The templates were in amounts of about 500 ng each. Primer #94 was present at 4 µM and primers #92 and #93 were present at 2 µM each. The primers were radiolabelled with $^{32}P$, at the 5'-terminus. The reactions were carried out in about 30 µM Tris-acetate at about pH 7.9, about 10 µM magnesium-acetate, about 10 µM dithiothereitol, and about 1.5 µM each, dATP, TTP, dCTP, dGTP. The total volume of the reaction was approximately 100 µl. The samples were heated to about 105° for 2 minutes, annealed at about 28° for 30 seconds and about 5 units of the Klenow fragment of DNA polymerase 1 from *E. coli* was added. The DNA polymerization continued for about 2 minutes. The heating, cooling and DNA polymerization cycle were repeated approximately 10 times. The reaction products were analyzed by electrophoresis on a 4% NuSieve agarose gel, followed by autoradiography.

Figure 3A:
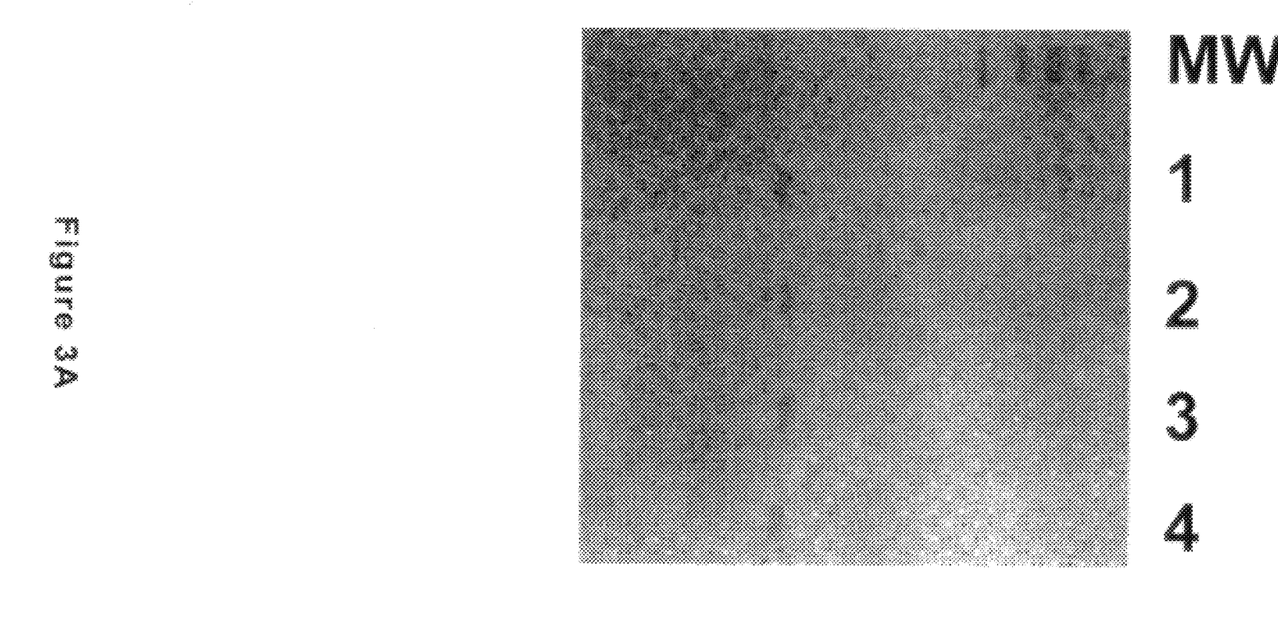
FIG. 3A demonstrates the analysis of competitive oligonucleotide priming products generated from primers specific to + and spf OTC alleles.

Each reaction generated a 72 bp fragment that corresponded to the region between primers #94 and either #92 or #93 (FIG. 3A). Each lane contains the product of 10 cycles of PCR amplification using either (+) OTC cloned cDNA (lanes 1 & 2) or spf OTC cloned cDNA (lanes 3 & 4). Lanes 1 and 3 contained radiolabeled primers specific to (+) OTC cDNA, lanes 2 and 4 contained radiolabeled primers specific for spf OTC cDNA. The COP event has been amplified into a 72 bp product by PCR amplification.

Figure 3B:
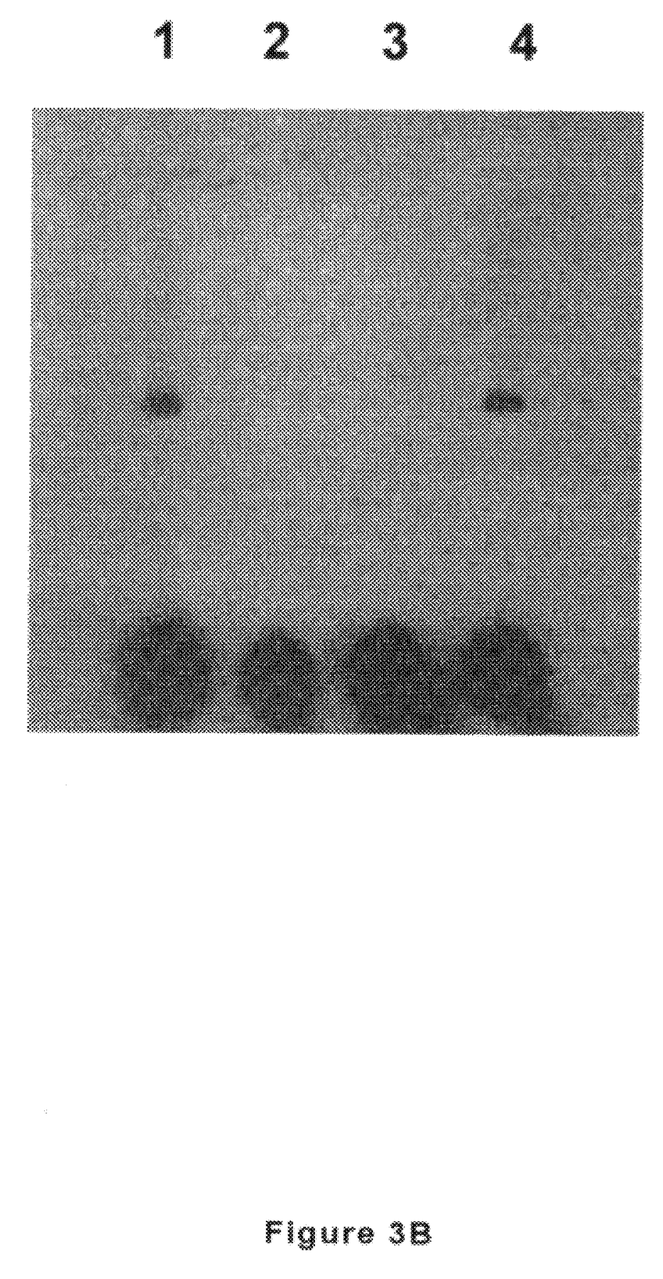
FIG. 3B shows autoradiographs of the gel shown in 3A demonstrating that the radioactive primers have been incorporated into a 72 nucleotide fragment in lanes 1 and 4, where the radioactive primers perfectly match the template, while the radioactive mismatch primers in lanes 2 and 3 have been excluded.

The presence of the 72 bp fragment in each reaction shows that efficient extension of oligonucleotide primers at each of the expected positions occurred and that amplification had been achieved. Autoradiographic analysis of the agarose gel revealed preferential utilization of the perfectly matched primers at sites where the two competing primers might bind (FIG. 3B). Thus, reactions (1) and (4) showed incorporation of radioactivity into the reaction product and conversely, reactions (2) and (3) had no radioactivity incorporated into the reaction product. The level of discrimination of the assay, that is, the degree of preferential utilization of the correctly matched primer over and above the mismatch primer, is demonstrated in FIG. 3B. Where the radioactivity is expected to be incorporated the radioactive signal is greater than 100 times the case where the radioactivity is expected to be excluded.

EXAMPLE 2

COMPETITIVE OLIGONUCLEOTIDE PRIMING BY USING PRIMERS TO SEQUENCES FROM M13 mp18 FILAMENTOUS PHAGE DNA.

To further illustrate the COP principle, and to investigate the effectiveness of the length of the competing oligomers on the COP phenomena, experiments were conducted using single stranded DNA template derived from the filamentous phage, M13mp18. The useful feature of mp18 is that it contains a region of DNA that has within its sequence the recognition sites for cleavage by a number of restriction endonucleases. When mp18 is faithfully copied by DNA synthesis, the restriction endonuclease recognition sites are reproduced. Aberrant DNA reproduction, such as when a mismatched DNA primer is incorporated, will destroy the restriction endonuclease recognition sites and prevent cleavage by those enzymes. When two primers are simultaneously provided as primers for DNA synthesis using mp18 as a DNA template, one primer being perfectly complementary to the template and one primer containing a single DNA base change that destroys a restriction endonuclease recognition site, the relative utilization of each of the two primers in the DNA synthesis reaction may be determined by the activity of the restriction endonuclease on the synthesis product. This example demonstrates that perfectly matched 12-mer oligomers (A) and 20-mer oligomers (B) each can be used to copy mp18 DNA and to produce a synthesis product that contains the originally present restriction endonuclease recognition sites. Next, the 12-mers or the 20-mers were mixed with other oligonucleotide primers that were identical, except for the presence of single DNA base substitutions that destroy restriction endonuclease recognition sequences, and then the DNA synthesis reactions were performed. When the primer mixture contained 12-mers, the perfectly matched oligomer was predominantly incorporated in the DNA synthesis reaction, as revealed by the persistence of restriction endonuclease recognition sites in the DNA synthesis products. The competition effect was diminished where the oligomer primers were 20-mers. Thus, under the conditions used here, 12-mer primers exhibit more effective COP than 20-mers.

A. Competitive Oligonucleotide Primary With mp18 and 12-mers

In this example the DNA template was a single stranded DNA from the filamentous phage M13 Mp18 (mp18). Three primers were used to demonstrate the competitive oligonucleotide primary method. A 12-mer primer, #85, which was perfectly complementary to a region of the mp18 DNA template containing the restriction endonuclease recognition sites for RsaI and MspI, was synthesized. A 12-mer primer, #86, was synthesized using mixed-coupling functions on an oligonucleotide synthesizer. Primer #86 is identical to primer #85 except that at two nucleotide positions within the #86 sequence, a pair of DNA bases was added during synthesis. Thus, the #86 "family" was composed of approximately 25% AGCTCGGTACCC, 25% AGCTCGGTACGC, 25% AGCTCGGAACCC, and 25% AGCTCGGAACGC. The base substitutions at the two positions were employed to represent family members which were either (a) perfectly complementary to the mp18 template, or (b) if hybridized to the mp18 template would generate a reaction product that no longer possessed the correct DNA sequence for recognition and cleavage by the restriction endonucleases RsaI or MspI. A 15-mer primer, #1, complementary to the mp18 DNA, in an opposite sense to, and approximately 75 base pairs from, the #85 and #86 binding sites was also synthesized. Primer #1 was the common oligonucleotide primer. Primer #1 was radiolabelled $^{32}$P at the 5'-terminus. The sequence of the primers is shown in Table 1. The DNA sequence of the region surrounding the primer binding sites is shown in FIG. 2A.

Two reactions were performed. Each contained about 500 ng of mp18 DNA template, about 4 µM radiolabelled primer #1 in about 30 µM Tris-acetate at about pH 7.4, about 50 µM sodium acetate, about 10 µM magnesium acetate, about 10 µM dithiothreitol, and about 1.5 µM each of dATP, TTP, dCTP, dGTP the total volume was approximately 100 µl. One reaction contained primer #85 and the other contained primer family #86. The reaction mixtures were heated to about 105° for about 2 minutes, cooled to about 28° for about 30 seconds, about 5 units of the large fragment of DNA polymerase 1 from *E. coli* were added and DNA polymerization carried out at about 28° for about 2 minutes. The heating, annealing and DNA polymerization were repeated 10 times. Aliquots of each reaction were taken following 5 and 10 rounds of the amplification, and either analyzed directly by gel electrophoresis and autoradiography or treated with a restriction endonuclease and then analyzed by gel electrophoresis and autoradiography.

Figure 4A:
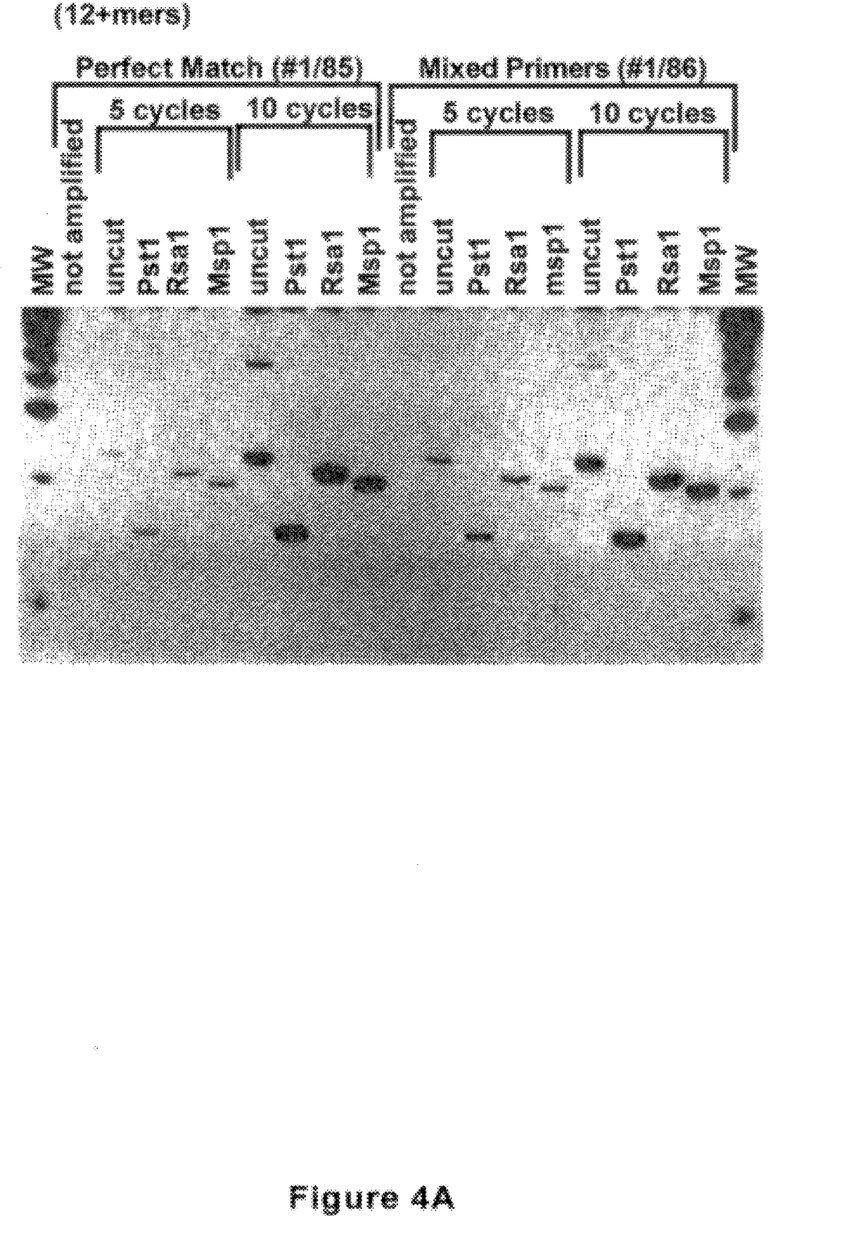
FIG. 4A demonstrates the autoradiographic analysis of fragments generated from COP and PCR of M13mp18 DNA using 12-mer oligonucleotides in the competition.

FIG. 4A shows that the material which was not treated with restriction endonuclease (un-cut) is represented by an 85 bp fragment. The 85 bp fragment is radioactive because it includes primer #1. When samples from the first reaction, containing primer #85, were treated with the restriction endonuclease PstI which recognizes and cleaves the DNA sequence between the binding sites for primer #1 and primer #85, then as expected a radiolabelled 48 bp product is generated. Since the PstI recognition sequence is between the oligonucleotide primers and should have been faithfully copied during successive rounds of DNA synthesis, the PstI treated sample serves as a control.

When samples from the first reaction containing primer #85 were treated with the restriction endonuclease RsaI or MspI, the expected radiolabelled 76 bp and 75 bp fragments were generated, FIG. 4A. The presence of the RsaI and MspI restriction endonuclease recognition sequence indicates that primer #85 had been faithfully incorporated during the successive rounds of DNA synthesis.

When the products of the second reaction, containing primer family #86 were analyzed in the same manner, a similar result was observed (FIG. 4A). That is, restriction endonuclease PstI cleaved a 48 bp fragment, showing that the region between primers #1 and the primer family #86 was faithfully copied during successive rounds of DNA synthesis. However, with RsaI or MspI, complete cleavage of the 85 bp fragment was also observed. This result indicates that a single member of the four member primer #86 oligonucleotide family was preferentially incorporated during the successive rounds of DNA synthesis. The failure to incorporate any of the other three family members that contained DNA base mismatches demonstrates the effective competition of a perfectly matched primer with other primers that are not perfect matches for the DNA template.

B. Competitive Oligonucleotide Priming With mp18 and 20-mers

This method using 20 mer oligomers is conceptually similar to the example above, using 12-mers.

Again a single stranded DNA from the filamentous phage M13 mp18 was used as the template. Three primers were used to demonstrate the competitive oligonucleotide primer method. A 20 mer primer, #89, was used which was a perfect match for a region of mp18 DNA template containing the restriction endonuclease recognition sites. for SacI, RsaI, and MspI. A 20-mer primer, #90, oligonucleotide "family", was synthesized using mixed-coupling functions on an oligonucleotide synthesizer. Primer #90 is similar to primer #89 except that at three positions within the #90 sequence a pair of DNA bases was added during synthesis. Thus, the #90 oligonucleotide family has eight members, 1 containing DNA sequences recognized by all 3 restriction endonucleases, 3 containing combinations of 2 sites, 3 containing 1 site and 1 having no restriction sites. Furthermore, each site is equally represented by a perfect match for the mp18 DNA template. The 15-mer primer, #1, was employed as the common primer. The sequence of the primers is shown in Table 1. The DNA sequence surrounding the primer binding sites is shown in FIG. 2A. The conditions for each reaction were the same in those used above in the competitive oligonucleotide priming of mp18 with 12-mers.

Figure 4B:
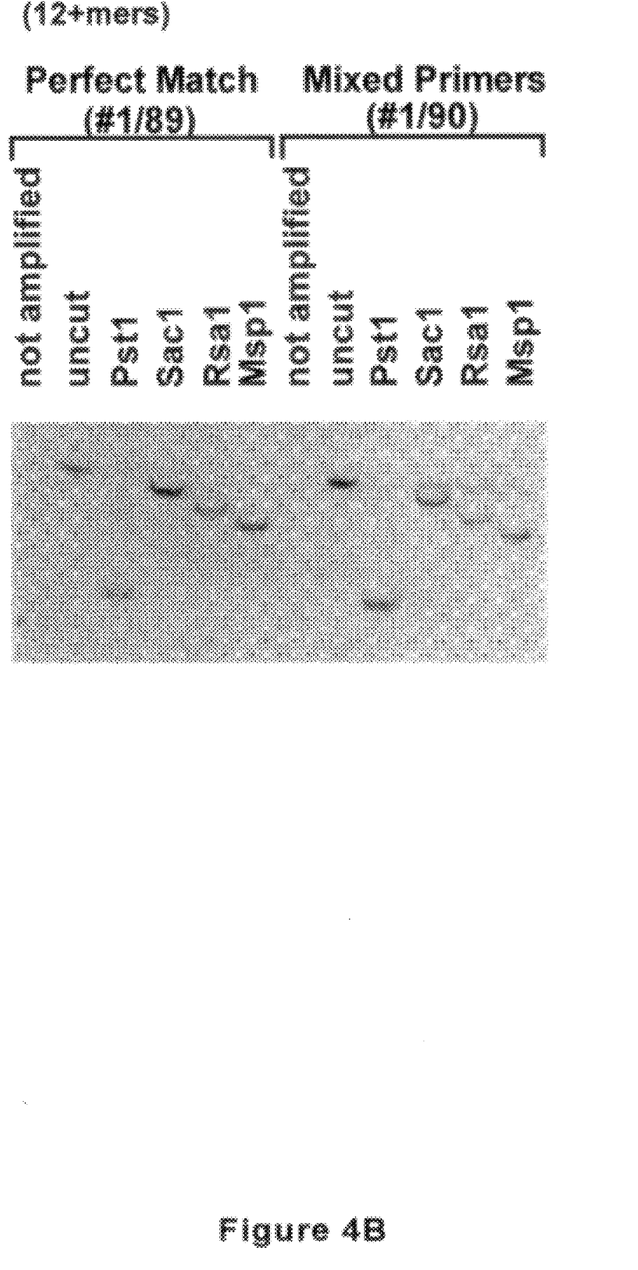
FIG. 4B demonstrates the autoradiographic analysis of fragments generated from COP and PCR of M13mp18 DNA using 20-mer oligonucleotides in the competition.

When samples from the reactions containing primer #89 were taken following 10 cycles of DNA synthesis and treated with the restriction endonucleases PstI, SacI, RsaI or MspI, then a 91 bp radiolabelled fragment was observed that could be reduced to 81, 76, or 75 bp's by the restriction endonucleases, respectively. (FIG. 4B). This indicated that both the region between the primers #1 and 89 and the DNA sequences overlapped by primer number 89 were faithfully copied during the repeated rounds of DNA synthesis.

In contrast, some of the products of the reaction containing the oligonucleotide primer family #90 were refractory to cleavage by the restriction endonucleases SacI, RsaI and MspI (FIG. 4B). The restriction endonuclease PstI that recognizes DNA sequences between the oligonucleotide priming sites, efficiently cleaved the reaction product. The failure to cleave was therefore due to the incorporation of the mismatched oligonucleotides from the #90 oligonucleotide family. Thus, while the experiment with mp18 DNA and 12 mers, Example 2(A) above, illustrates that, under these reaction conditions, 12 mers may exhibit effective competition for a unique DNA priming site, longer (20 mer) oligomers may exhibit less effective competitive oligonucleotide priming.

EXAMPLE 3

β$^s$-GLOBIN (SICKLE CELL ALLELE)

The mutation in humans causing sickle cell anemia is also detectable by competitive oligonucleotide priming. The normal DNA sequence (β$^+$) of the human β-globin gene in the region of the β-sickle cell allele is:

And the site of the single DNA base change that gives rise to the β$^s$ (Sickle Cell) hemoglobinopathy is indicated by an arrow. The base change leading to the β$^s$ genotype is A→T. Thus, the following primers can be constructed and used in the competitive oligonucleotide primer assay:

(1) 5'-CTC.CTG.AGG.AGA.-3' (12-mer -β$^+$ specific)
(2) 5'-CTC.CTG.TGG.AGA.-3' (12-mer - β$^s$ specific)

Primers (1) and (2) can be differentially labelled and then used simultaneously in a COP reaction with either cloned β$^+$-globin or β$^s$-globin sequences.

The successfully competing primer is then identified using a third primer to amplify the extension product of the competitive primer which successfully bound the DNA:

(3) 5'-CGT.TCA.CCT.TGC.CCC.ACA.GG-3'

Primer 3 will prime DNA synthesis in an opposite direction to primers 1 or 2. When this assay is performed using the primer trio 1, 2 and 3, then a 47 bp fragment is produced and would indicate the true DNA sequence of the DNA template.

If the starting material to assay was a complex DNA mixture, e.g. human genomic DNA, then two primers may be first used to amplify the site containing the β$^s$ mutant allele.

For example, the oligonucleotides

5'-TGG.TCT.CCT.TAA.ACC.TGT.CTT.G-3'

5'-ACA.CAA.CTG.TGT.TCA.CTA.G-3' amplify a 167 bp segment of the human β-globin gene, containing DNA complementary to primers 1, 2 and 3 described herein.

Following amplification of the region containing the $\beta^s$ mutation, the competitive oligonucleotide primer assay can be performed as described above. In each case, the oligomers corresponding to either the $B^+$ or $B^s$ alleles would be labeled, so as to be distinguished from the other oligomers. The detection of the unique label is the end point of the assay.

EXAMPLE 4

$\alpha_1$-ANTITRYPSIN Z ALLELE; S ALLELE

The mutations in humans leading to deficiency of $\alpha_1$-antitrypsin is also detectable by competitive oligonucleotide priming. The normal human DNA sequence (M) in the $\alpha_1$-antitrypsin gene, surrounding the site containing the $\alpha_1$-Z allele is:

and the mutation shown at the arrow (G→A) gives rise to the mutant Z allele.

Similarly, the normal human DNA sequence (M) in the $\alpha_1$ antitrypsin gene, surrounding the site containing the $\alpha_1$-S allele is:

and the mutation shown (A→T) gives rise to the S allele.

Thus, primers specific for the discrimination of the M/Z allele pair or the M/S allele pair can be constructed:

(A) M/Z (1) 5'-ATC.GAC.GAG.AAA.-3' (M) (2) 5'-ATC.GAC.AAG.AAA.-3' (Z)

(B) M/S (3) 5'-ACC.TGG.AAA.ATG.-3' (M) (4) 5'-ACC.TGG.TAA.ATG.-3' (S)

Primers (1) and (2), and (3) and (4) can be differentially labeled and used in the competitive oligonucleotide primer assay to distinguish cloned normal (M) or mutant (Z or S) $\alpha_1$-antitrypsin DNA sequences. The extension products of the successfully competing primers can be detected, after amplification, through the use of common primers.

For example, primers (1) and (2) plus primer (5) (5'-CAG.CCA.GCT.TCA.GTC.CCT.TTC-3') will together produce a fragment of 81 bp in the reaction. Primers (3) and (4) plus primer (6) (5'-GGG.AAT.CAC.CTT.CTG.TCT.TC-3') will produce a fragment of 70 bp.

If the starting material includes samples of human genomic DNA, then the primer sets, 5'-ACG.TGG.AGT.GAC.GAT.GCT.CTT.CCC-3' and 5'-GTG.GGA.TTC.ACC.ACT.TTT.CCC-3', that flank but do not include the mutation site for the Z allele can be employed to preamplify a 450 bp fragment of the $\alpha_1$-antitrypsin gene containing the Z allele. Primer sets 5'-GAA.GTC.AAG.GAC.ACC.GAG.GAA-3' and 5'-AGC.CCT.CTG.GCC.AGT.CCT.AGT.G-3' which flank but do not include the mutation site for the S allele may be employed to preamplify a 340 bp region of the $\alpha_1$-antitrypsin gene containing the S allele.

The amplified mutation sites could then be utilized as starting material for the COP analysis using the competitive oligonucleotides and their opposing common primers. For instance, primers (1) and (2) compete to bind to the site of the Z allele within the amplified 450 bp fragment. The extension product of the successfully competing primer, either (1) or (2), can then be detected after amplification through the use of the common primer (5). Similarly, primers (3) and (4) compete to bind to the site of the S allele within the 340 bp fragment and the extension product of the successfully competing primer, either (3) or (4), detected after amplification through the use of the common primer (6).

One skilled in the art will readily appreciate the present invention is well adapted to carry out the objects and obtain the ends and advantages mentioned, as well as, those inherent therein. The methods, procedures and techniques described herein are presently representative of the preferred embodiments, are intended to be exemplary, and are not intended as limitations on the scope. Changes therein and other uses will occur to those skilled in the art which are encompassed within the spirit of the invention or defined by the scope of the appended claims.

What is claimed is:

1. A method for detecting the presence or absence of a specific known nucleic acid sequence, or distinguishing between different sequences, comprising the steps of:

adding competitive oligonucleotide primers to a sample of nucleic acid or mixture of nucleic acids wherein at least some of the nucleic acids are polynucleotides comprising a specific known sequence, wherein said competitive oligonucleotide primers include at least two primers, a first primer being substantially complementary to the specific known sequence and at least a second primer having a base mismatch with the specific known sequence;

preferentially hybridizing the first primer to the specific known sequence under competitive conditions to form a preferentially hybridized primer complex, said complex comprising a polynucleotide comprising the specific known sequence, and the first primer, the first primer being hybridized to the polynucleotide at the specific known sequence;

extending the preferentially hybridized primer from its 3' terminus to synthesize an extension product, said extension product being complementary to the polynucleotide comprising the specific known sequence; and identifying and detecting the presence or absence of said extension product as an indication of the presence of absence of said specific known sequence.

2. The method of claim 1, wherein said competitive oligonucleotide primers are about 8 to about 24 nucleic acids.

3. The method of claim 1, wherein at least one of said competitive oligonucleotides primers is labeled and said extension product is identified by determining the presence or absence of said label in said extension product.

4. The method of claim 3, wherein said label is selected from the group consisting of radioisotopes, fluorescers, chemiluminescers, enzymes and antibodies.

5. The method of claim 1 comprising the further steps of:

adding a common oligonucleotide primer prior to identifying and detecting said extension product;

separating said extension product from its complementary strand; and repeating said preferentially hybridizing and said extending steps.

6. The method of claim 5, comprising the further step of repeating at least once, said separating, preferentially hybridizing and extending steps.

7. A competitive oligonucleotide primer method for detecting the presence or absence of a specific known nucleic acid sequence in a sample containing a mixture of complementary nucleic acid strands, or distinguishing between at least two different sequences in the sample, comprising the steps of:

adding a common primer and competitive oligonucleotide primers to a sample of nucleic acid or mixture of nucleic acids wherein at least some of the nucleic acids are specific known sequence polynucleotides which are polynucleotides comprising a specific known sequence, wherein said competitive oligonucleotide primers include at least first and second primers, the first primer being substantially complementary to the specific known sequence in said specific known sequence polynucleotide and at least the second primer having a base mismatch with the specific known sequence, and said common primer is complementary to a common sequence in a complementary polynucleotide that is complementary to said specific known sequence polynuclotide, and said common sequence in said complementary polynucleotide is at a site distant from a site on the complementary polynucleotide that is complementary to the specific known sequence;

annealing said first primer to said specific known sequence in said specific known sequence polynucleotide, and annealing said common nucleotide primer to said common sequence in said complementary polynucleotide under conditions in which said common primer anneals to said common sequence in said complementary polynucleotide and said first primer anneals to said known specific sequence in said known sequence polynucleotide to form a first primer/specific known sequence complex and a second primer/common sequence complex;

extending the primers, from the first primer/specific known sequence complex and second primer/common sequence complex, from the 3' terminus to synthesize a first primer extension product, and a second primer extension product;

separating said first and second extension products from their templates to produce first and second single-stranded molecules;

amplifying said single-stranded first and second molecules by repeating, at least once, said annealing, extending and separating steps; and identifying and detecting the presence or absence of said extension products as an indication of the presence of absence of said specific known sequence.

8. The method of claim 7, wherein at least one of said competitive oligonucleotides primers is labeled with a label selected from the group consisting of radioisotopes, fluorescers, chemiluminescers, enzymes and antibodies.

9. The method of claim 8, wherein said identifying step includes detecting the presence or absence of said label in the amplified extension product.

10. The method of claim 8, wherein said common oligonucleotide primer is bound to a solid support, and said amplified extension product is identified by measuring the presence or absence of said label attached to said solid support.

11. The method of claim 7, wherein said specific nucleic acid sequence contains at least one mutation that causes a genetic disease.

12. A competitive oligonucleotide primer method for detecting the presence or absence of a plurality of specific known nucleic acid sequences in a sample containing a mixture of nucleic acid strands, comprising the steps of:

providing a plurality of primers, wherein individual primers comprise nucleic acid sequences complementary to a plurality of specific known nucleic acid sequences present on a plurality of template nucleic acid strands, each individual strand comprising at least one specific known nucleic acid sequence;

annealing specific oligonucleotide primers to each specific known sequence thereby creating a plurality of annealed primer/nucleic acid strand complexes wherein the primer and the nucleic acid strand are annealed at a region of complementary nucleic acid sequence;

extending each of said annealed primer/nucleic acid strand complexes from the 3' terminus of the primer to synthesize a plurality of extension products, each complementary to its corresponding template strand;

separating said primer extension products from said templates on which they were synthesized to produce single-stranded molecules; said extension products, after separation serving as templates for synthesis of additional extension products of said specific oligonucleotide primers;

amplifying said single-stranded molecules comprising said specific known sequences by repeating, at least once, said annealing, extending and separating steps;

adding competitive oligonucleotide primers to said sample, wherein said competitive oligonucleotide primers include at least two primers for each specific known sequence, a first competitive primer being substantially complementary to said specific known sequence and at least a second competitive primer having a base mismatch which the specific known sequence;

preferentially hybridizing said first competitive primers to said specific known sequences under competitive conditions to form competitive primer complexes;

extending the first competitive primer from the competitive primer complex from the 3' terminus of said primer to synthesize competitive extension products complementary to said template nucleic acid strands; and identifying and detecting the presence or absence of said competitive extension products as an indication of the presence of absence of said specific known nucleic acid sequence in said template nucleic acid strands.

13. The method of claim 12, wherein said competitive oligonucleotide primers are about 8 to about 24 nucleic acids long.

14. The method of claim 12, wherein at least one of said competitive oligonucleotide primers is labeled and said competitive extension product is identified by determining the presence or absence of said label in said competitive extension product.

15. The method of claim 14, wherein, the label is selected from the group consisting of radioisotopes, fluorescers, chemiluminescers, enzymes and antibodies.

16. The method of claim 12, comprising the further steps of:

adding a common oligonucleotide primer prior to said identifying step;

separating said competitive extension product from its complementary strand; and repeating said preferentially hybridizing and said extending steps.

17. The method of claim 16, comprising the further step of repeating at least once said separating, preferentially hybridizing and extending steps.

18. The method of claim 14, wherein, said common oligonucleotide primer is bound to a solid support and said amplified competitive extension product is identified by measuring the presence or absence of label on said solid support.

19. A competitive oligonucleotide primer method of detecting a genetic disease which results from at least one mutation in a specific known nucleic acid sequence, comprising the steps of:

adding competitive oligonucleotide primers to a sample of nucleic acid or a mixture of nucleic acids, wherein said competitive oligonucleotide primers include at least two competitive primers, a first primer being substantially complementary to a normal genetic sequence and at least one second primer being substantially complementary to a mutated genetic sequence;

preferentially hybridizing said first and second primers to the appropriate strands containing said normal genetic sequence and mutated genetic sequence under competitive conditions thereby forming preferentially hybridized primer complexes;

extending the primers from the preferentially hybridized primer complexes from the 3' terminus of the primers to synthesize extension products complementary to said normal genetic sequence and mutated genetic sequence strands to which the primers are hybridized; and identifying and detecting the presence or absence of said extension products as a measure of the presence of absence of said normal genetic sequence and mutated genetic sequence strands.

20. The method of claim 19, wherein at least one of said competitive oligonucleotide primers is labeled with a label selected from the group consisting of radioisotopes, fluorescers, chemiluminescers, enzymes and antibodies.

21. The method of claim 20, wherein each competitive oligonucleotide primer is differentially labelled.

22. The method of claim 20, comprising the further steps of:

dividing said sample into a plurality of portions prior to adding said competitive oligonucleotide primers;

adding a different, labeled competitive oligonucleotide primer to each of said portions; and measuring the presence or absence of said label in said extension products in each of said portion.

* * * * *